United States Patent [19]

Shinozawa

[11] 4,450,151

[45] May 22, 1984

[54] POWDER AEROSOL COMPOSITION

[75] Inventor: Takahiro Shinozawa, Tokyo, Japan

[73] Assignee: Toyo Aerosol Industry Co., Ltd., Tokyo, Japan

[21] Appl. No.: 47,910

[22] Filed: Jun. 12, 1979

[30] Foreign Application Priority Data

Aug. 21, 1978 [JP] Japan .................... 53-101559

[51] Int. Cl.³ .............................. A61K 9/12
[52] U.S. Cl. ........................ 424/46; 424/47; 424/65; 424/67; 424/230; 424/238
[58] Field of Search .............. 424/46, 47, 68

[56] References Cited

U.S. PATENT DOCUMENTS

| | | | |
|---|---|---|---|
| 3,014,844 | 12/1961 | Thiel et al. | 424/47 |
| 3,088,874 | 5/1963 | Geary et al. | 424/68 X |
| 3,574,822 | 4/1971 | Shepherd et al. | 424/46 |
| 4,110,427 | 8/1978 | Kalat | 424/46 |

FOREIGN PATENT DOCUMENTS

| | | | |
|---|---|---|---|
| 2503962 | 8/1976 | Fed. Rep. of Germany | 424/46 |
| 1372749 | 7/1964 | France | 424/46 |
| 2167914 | 8/1973 | France | 424/47 |
| 2267086 | 11/1975 | France | 424/46 |
| 2348263 | 10/1977 | France | 424/45 |
| 409 | 1/1966 | Japan . | |
| 14804 | 8/1967 | Japan . | |
| 798 | 1/1970 | Japan . | |
| 51-12593 | 4/1976 | Japan | 424/47 |
| 31024 | 8/1977 | Japan . | |
| 1813 | 1/1978 | Japan . | |
| 6613943 | 4/1968 | Netherlands | 424/47 |
| 698870 | 2/1970 | South Africa | 424/47 |
| 34352 | 2/1960 | Switzerland | 424/45 |
| 987301 | 3/1965 | United Kingdom | 424/46 |
| 1403139 | 8/1975 | United Kingdom | 424/46 |
| 1498123 | 1/1978 | United Kingdom | 424/46 |

*Primary Examiner*—Dale R. Ore
*Attorney, Agent, or Firm*—Parkhurst & Oliff

[57] ABSTRACT

A powder aerosol composition is obtained by first preparing a suspension consisting of a hydrophobic powdered substance having its pH adjusted to fall within the range 5 to 9, alcohol and water, adding, if required by the desired powder system, an intentional medicine and other auxiliary agents to the suspension and mixing the suspension with 5 to 40 wt % of a propellant in an aerosol container. The thusly produced composition has an improved safety in application, prevents flying properties, has an improved adhesion to the skin and can be produced inexpensively. Thus, the composition is best suited for use in applications such as baby powder, dry shampoo, water-eczema remedy and antiperspirant.

11 Claims, No Drawings

POWDER AEROSOL COMPOSITION

BACKGROUND OF THE INVENTION

The present invention relates to a powder aerosol composition.

Aerosol products consisting of powdered material suspended, along with a prime agent and auxiliary agents, in a liquefied freon gas for spraying purposes are known in the art and they include antiperspirant, water-eczema remedy, dry shampoo, baby powder, etc. However, these known products have great flying tendency and adhere to the skin only at a low rate, and moreover the liquefied freon gas has an agglomeration tendency when hydrophobic powder is suspended in it, thus making it difficult to mix a high proportion of such powder. Consequently, it is possible to add powdered substance and dispersant only to about 0.5 to 10 wt % of the total quantity and it is necessary to use liquefied freon gas in an amount greater than 80 wt % of the total quantity, thus making the resulting product very expensive. In addition, due to the use of the liquefied freon gas as the propellant, the known products are high in cost due to the high cost of the propellant and they also have a chilling action, thus sometimes causing frost-bite, inflammation or the like on the skin. Some studies have been made public to the effect that the use of freon gas is not desirable from the standpoint of air pollution.

SUMMARY OF THE INVENTION

With a view to overcoming the foregoing deficiencies of the prior art powder aerosol compositions, it is the object of the invention to provide an improved powder aerosol composition which can be produced inexpensively, is capable of minimizing sensation of coldness and occurrence of inflammation on the skin and ensuring an improved safety in use and is also capable of ensuring satisfactory drying properties upon adhesion to the skin while preventing flying properties, thus preventing stickiness and the like. Generally, if powder, water, alcohol, liquefied gas are mixed, the resulting suspension will be condensed due to a high concentration, thus deteriorating the redispersion properties and making it impossible to satisfactorily spray the suspension as an aerosol composition and thereby tending to cause clogging of the nozzle and the like. In accordance with the present invention, water, alcohol, powder and a liquefied gas (propellant) can be used to produce a satisfactory composition which overcomes the foregoing deficiencies in the prior art.

DESCRIPTION OF THE PREFERRED EMBODIMENTS

As mentioned previously, the present invention relates to a powder aerosol composition comprising a mixture of a suspension consisting of powdered material, alcohol, water, an intentional medicine added as occasions demand and other auxiliary agents with a propellant. The individual ingredients will be first described in detail in turn and then preferred examples will be described in comparison with comparative examples. The "powdered substance" will be described first.

A hydrophobic powdered substance having a pH value of 5 to 9 and a particle size of 70 to 325 mesh may be used as the powdered substance. One or more substances selected from the group consisting of talc, Celite, kaolin, red oxide, rice starch, bentonite, alumium stearate may be used as the hydrophobic powder. Since the pH value of this kind of powders is usually over 5, any powder having a pH of over 10 may be used by subjecting it to acid treatment to reduce the pH value to the range of 5 to 9. To use any hydrophobic powder falling outside the range pH 5 to 9 in the aerosol system as such is not desirable since the powder agglomerates in the aerosol container and clogs the valve. Although such hydrophobic powder falling outside of the pH range of 5 to 9 may be used by producing a stable suspension with the aid of a surface-active agent, this is not preferable in that spraying of the aerosol results in foaming thus causing an offensive feeling of application on the part of the user.

The desired powder pH value is limited to the range of 5 to 9 on the ground that it represents a necessary pH range whereby the powder can be satisfactorily dispersed and prevented from agglomerating in a liquid, such as alcohol and water which will be described later. Generally, none of the powders of the above-mentioned kind has a pH value of less than 4, and if the pH value is over 10 the degree of alkalinity will be excessively high with the result that the particles tend to agglomerate and sometimes secondary particles will be formed, thus causing clogging of the spray nozzle and making the spraying impossible and thereby making the substance unsuitable for use as the "powdered substance" of the invention.

The desired alcohol is one whose number of carbon atoms is in the range 1 to 7, and 95 vol % ethyl alcohol, isopropyl alcohol, etc., may be used.

A desired intentional medicine is suitably selected depending on the application of a powder system (formula) and it may for example be basic alumimum chloride, methyl salicylate, hydrocortisone, aluminum chlorohydroxide, cortisone sulfate, zinc undecylenic acid, menthol, etc. If necessary, as auxiliary agents, such an emollient as lanolin alcohol or isopropyl myristate and/or such germicide agent as Hyamine #1622 [Trade name of the product of ROHM AND HAAS, Philadelphia], Biosol (isopropylmethyl phenol) [Trade name of the product of Osaka Kasei Co., Ltd.], etc., may be suspended in the liquid comprising water and alcohol in addition to the powder. If the intentional medicine and the auxiliary medicine used are in powder form, they may be used in small quantities even if they are of the hydrophilic nature.

The propellant may comprise for example liquefied petroleum gas, dimethyl ether or the like gas which is lower in specific gravity than the suspension. The reason for requiring the use as the propellant of a liquefied gas which is lower in specific gravity than the suspension resides in that in this way the propellant must be placed above the remaining contents in the aerosol container so as to facilitate propelling of the contents other than the propellant (i.e., the suspension) through the dip tube.

The suspension is prepared by mixing together in a homomixer 5 to 60 wt % (preferably 20 to 30 wt %) of a hydrophobic powder having a pH value of 5 to 9 and particle size of 70 to 325 mesh, 5 to 80 wt % (preferably in the range 25 to 35 wt %) of alcohol whose number of carbon atoms is in the range 1 to 7, 5 to 80 wt % (preferably in the range 30 to 40 wt %) of water as well as an intentional medicine and such auxiliary agents as emollient medicine and germicide which are added in suitable quantities in dependence on the desired "powder system". In this case, the resulting suspension has a viscosity of 50 CPS to 1000 CPS and pH value of 5 to 9. If a suspension is prepared by mixing together the ingredients in their preferred proportions, the suspension will have a viscosity in the range of 100 CPS to 400 CPS and pH value in the range 5.5 to 7.5. This suspension is placed in an aerosol container along with a propellant such as liquefied petroleum gas or dimethyl ether which is lower in specific gravity than the suspension.

In accordance with the invention, since liquefied petroleum gas, dimethyl ether or the like is used as the propellant as mentioned above, it is possible to provide the desired product inexpensively, and moreover the addition of water has the effect of ensuring reduced flammability even if the propellant is highly flammable. Also, due to the addition of water, the hydrophobic particles slightly absorb the water and the adhesion of the particles to the skin is improved, thus reducing the percentage of fly loss and thereby ensuring excellent feeling of application and making the product economical. Further, since the water mixes with the alcohol added to the powder system, when the integrally mixed alcohol and water are sprayed from the nozzle, the vaporization and evaporation of the propellant cause the alcohol and water to rapidly evaporate until they reach the skin, with the result that there is left only a small amount of the water necessary for the improved adhesion and consequently the particles are allowed to stick to the skin in a dry state. Still further, since the pH value of the powder is in the range pH 5 to 9, the particles slightly absorb the alcohol and water in the suspension, so that the particles are dispersed satisfactorily in the suspension and there is no possibility of forming any agglomerate. Thus, there is no danger of causing clogging of the valve and the like, and an improved stability during manufacture, storage, etc., is also ensured. Still further, since the hydrophobic particles have no tendency to agglomerate, the proportion of the suspension to the propellant can be increased greatly, that is, it is possible to make the proportion of the suspension consisting of alcohol, water and hydrophobic powder less than 95 wt %, preferably in the range 70 to 80 wt % and that of the propellant over 5%, preferably in the range 20 to 30%, and these proportions ensure a stable powder aerosol composition. With the thusly produced composition, the occurrence of such phenomena as precipitation, swimming, condensation, etc., of the hydrophobic particles as well as the intentional medicine are very rare even if the composition is left to stand for a long period of time. Although a slight precipitation phenomenon may be caused depending on the kind and preparation conditions of hydrophobic powder, intentional medicine, etc., there is no possibility of any high condensation as in the case of the known compositions employing liquefied freon gas, and the composition can be easily brought back to the uniform suspension by shaking the composition only one or two times.

The following table shows a series of examples. The kinds of compositions produced in the examples listed in the Table are as follows.

| Example | Kind of Composition |
|---|---|
| 1 | Powder |
| 2 | Powder |
| 3 | Powder |
| 4 | Powder |
| 5 | Powder |
| 6 | Powder |
| 7 | Powder |
| 8 | Powder |
| 9 | Dermatic medicine |
| 10 | Antiperspirant |
| 11 | Dermatic medicine |
| 12 | Antiperspirant |
| 13 | Water-eczema remedy |
| 14 | Dermatic medicine |
| 15 | Dry shampoo |
| 16 | Antiperspirant |
| 17 | Water-eczema remedy |
| 18 | Powder |
| 19 | Powder |
| 20 | Powder |
| 21 | Powder |
| 22 | Powder |
| 23 | Powder |
| 24 | Powder |
| 25 | Powder |
| 26 | Dermatic medicine |
| 27 | Antiperspirant |
| 28 | Dermatic medicine |
| 29 | Antiperspirant |
| 30 | Water-eczema remedy |
| 31 | Dermatic medicine |
| 32 | Dry shampoo |
| 33 | Antiperspirant |
| 34 | Water-eczema remedy |
| 35 | Antiperspirant |
| 36 | Dry shampoo |
| 37 | Dry shampoo |
| 38 | Dermatic medicine |
| 39 | Shoe deodorant |
| 40 | Water-eczema remedy |
| 41 | Powder |
| 42 | Powder |

In the Table, the examples 18 to 42 represent the compositions produced according to the invention and the examples 1 to 17 are those made for the purpose of comparison with the invention. The redispersion properties of the examples represent the dispersion properties observed after the compositions were left to stand for 3 months in an atmosphere of 45° C., and the mark ◎ indicates uniform dispersion properties, Δ high agglomerating tendency and X those involving at least a severe agglomeration in part.

| | | Example (in wt %) | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Powder | Talc (pH 10) | 25 | | | | | | | | | | | | | | |
| | Talc (pH 11) | | 23 | 25 | 25 | 30 | 30 | | 25 | 18 | 15 | 20 | 20 | 18 | 18 | 18 |
| | Talc (pH 6.0) | | | | | | | 15 | | | | | | | | |
| | Talc (pH 7.5) | | | | | | | 0.5 | | | | | | | | |
| | Celite (pH 10) | | 5 | | 5 | | | 10 | 5 | 5 | 10 | 10 | 10 | 5 | 5 | 5 |
| | Celite (pH 5.5) | | | | | | | | | | | 1 | | | | |
| | Kaolin (pH 6) | | | | | | 2.5 | | | | 2.5 | 2.5 | | | | |
| | Red oxide (pH 7) | | | | 0.5 | | | | 2.5 | | | | | 5 | | |
| | Rice starch (pH 7) | | | | | | | | | | | | | | | 2 |
| | Bentonite (pH 6) | | | | | | | | 0.5 | | | | | | | |
| | Aluminum stearate (pH 7) | | | | | | | | | | | | | | | |
| Deionized water | | 30 | 30 | 30 | 30 | 25 | 20 | 35 | 20 | 20 | 30 | 25 | 30 | 20 | 30 | 30 |
| Alcohol | 95 vol % ethyl alcohol | 30 | 30 | 30 | 30 | 30 | 25 | 25 | 15 | 25 | 28 | 25 | 25 | 20 | 25 | 28 |
| | isopropyl alcohol | | | 15 | | | | | | | | | | | | |
| Emollient | Lanolin alcohol | | | | | | | | | | | | | | | |
| medicine | Isopropyl myristate | | | | | | | | 0.1 | | | | 0.2 | | | |
| Germicide | Hyamine #=1622 | | 0.1 | | | | | | 0.2 | | | | | | | |
| | Biosol (isopropylmethyl phenol) | | | | | | | | | 0.1 | | | | | | |
| Intentional prime medicine | Basic aluminum chloride | | | | | | | | | | | | 0.3 | 1 | | |
| | Methyl salicylate | | | | | | | | | | | | | | | |
| | Hydrocortisone | | | | | | | | | 0.9 | | | | | | |
| | Aluminum chlorohydroxide | | | | | | | | | | | | | | | |
| | Cortisone sulfate | | | | | | | | | | 5 | | | | | |
| | Zinc undecylenic acid | | | | | | | | | | | | | | 0.1 | |
| | Menthol | | | | | | | | | | | | | | | 0.1 |
| Propellant | LPG | 15 | 12 | 15 | | 15 | 22.5 | 14.5 | 31.7 | 31 | 9.5 | 16.5 | 9.5 | 32 | 21.9 | 16.9 |
| | Dimethyl ether | | | | 9.5 | | | | | | | | | | | |
| Total | | 100 | 100 | 100 | 100 | 100 | 100 | 100 | 100 | 100 | 100 | 100 | 100 | 100 | 100 | 100 |
| Redispersion properties | | X | X | X | X | X | X | △ | X | X | X | △ | X | X | X | X |

| | | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| Powder | Talc (pH 10) | 18 | 18 | | | | | | | | | | | | | |
| | Talc (pH 11) | | | 25 | 23 | 25 | 25 | 30 | 30 | | 25 | 18 | 15 | | 20 | 18 |
| | Talc (pH 6.0) | | | | | | | | | | | | 20 | 20 | | |
| | Talc (pH 7.5) | | | | | | | | | 0.5 | | | 1 | | | |
| | Celite (pH 10) | | 5 | | 5 | | 5 | | | 15 | 5 | 5 | 10 | 10 | 10 | 5 |
| | Celite (pH 5.5) | | | | | | | | | 10 | 2.5 | | | 2.5 | | |
| | Kaolin (pH 6) | 1 | | | | | 0.5 | | | | 0.5 | | | | | |
| | Red oxide (pH 7) | 35 | | | | | | | 2.5 | | | | | | | 5 |
| | Rice starch (pH 7) | 25 | | | | | | | | | | | | | 5 | |
| | Bentonite (pH 6) | | | | | | | | | | | | | | | |
| | Aluminum stearate (pH 7) | 0.1 | | | | | | | | | | | | | | |
| Deionized water | | | 25 | 30 | 30 | 30 | 25 | 25 | 20 | 35 | 20 | 20 | 30 | 24.8 | 30 | 20 |
| Alcohol | 95 vol % ethyl alcohol | | 30 | 30 | 30 | 30 | 25 | 30 | 15 | 25 | 15 | 25 | 28 | 25 | 25 | 20 |
| | isopropyl alcohol | | | | | | | | 25 | | | | | | | |
| Emollient | Lanolin alcohol | | | | | | | | | | 0.1 | | | | | |
| medicine | Isopropyl myristate | | | | | | | | | | 0.2 | | | 0.2 | 0.2 | |
| Germicide | Hyamine #=1622 | | 0.1 | | | | | | | | | 0.1 | | | | |
| | Biosol (isopropylmethyl phenol) | | | | | | | | | | | | | | | |

-continued

| | | Example (in wt %) | | | | | | | | | | |
|---|---|---|---|---|---|---|---|---|---|---|---|---|
| | | 31 | 32 | 33 | 34 | 35 | 36 | 37 | 38 | 39 | 40 | 41 | 42 |
| Intentional prime medicine | Basic aluminum chloride | 20.9 | 20.9 | | | | | | | | | | |
| | Methyl salicylate | | | | | | | | | | | 0.9 | |
| | Hydrocortisone | | | | | | | | | | | | |
| | Aluminum chlorohydroxide | | | | | | | | | | | | |
| | Cortisone sulfate | | 1 | | | | | | | | | | 5 |
| | Zinc undecylenic acid | | | | | | | | | | | | |
| | Menthol | | | | | | | | | | | | 0.3 |
| Propellant | LPG | | | 15 | 12 | 15 | 9.5 | 15 | 22.5 | 14.5 | 31.7 | 31 | 9.5 | 16.5 | 0.3 |
| | Dimethyl ether | | | | | | | | | | | | | 1 |
| | Total | 100 | 100 | 100 | 100 | 100 | 100 | 100 | 100 | 100 | 100 | 100 | 100 |
| Redispersion properties | | X | X | ⊙ | ⊙ | ⊙ | ⊙ | ⊙ | ⊙ | ⊙ | ⊙ | ⊙ | ⊙ |

| | | Example (in wt %) | | | | | | | | | | |
|---|---|---|---|---|---|---|---|---|---|---|---|---|
| | | 31 | 32 | 33 | 34 | 35 | 36 | 37 | 38 | 39 | 40 | 41 | 42 |
| Powder | Talc (pH 10) | 18 | 18 | 18 | 18 | | | | | | | | |
| | Talc (pH 11) | | | | | | | | | | 4 | 5 | 5 |
| | Talc (pH 6.0) | | | | | 5 | 10 | 15 | | 5 | | | |
| | Talc (pH 7.5) | | | | | | | 2 | | | | | |
| | Celite (pH 10) | 5 | 5 | | 5 | 18 | 18 | | 20 | 30 | 25 | 18 | 22 |
| | Celite (pH 5.5) | | | | | | | | 5 | | | 7 | |
| | Kaolin (pH 6) | | 2 | | | | 5 | | | | | | |
| | Red oxide (pH 7) | | | 1 | | | | | | | | 0.7 | |
| | Rice starch (pH 7) | 30 | 30 | 35 | 25 | 25 | 20 | 25 | 25 | 25 | 20 | 20 | 30 |
| | Bentonite (pH 6) | 25 | 28 | 25 | 30 | 30 | 25 | 25 | 28 | 28 | 22 | 29 | 25 |
| | Aluminum stearate (pH 7) | | | | | | | | | | | | 0.7 |
| Deionized water | | | | | | | | | | | | | 0.2 |
| Alcohol | 95 vol % ethyl alcohol | | | | | | | | | | | | |
| | Isopropyl alcohol | | | | | | | | | | | | |
| Emollient medicine | Lanolin alcohol | | | | | | | | | | 0.2 | 0.1 | |
| | Isopropyl myristate | | | | | | | | | | | | |
| Germicide | Hyamine #=1622 | | | | 0.1 | 0.2 0.9 | 0.2 | 0.2 | 0.2 | 0.1 | | | |
| | Biosol (isopropylmethyl phenol) | | | | | | | | | | | | |
| Intentional prime medicine | Basic aluminum chloride | | | 0.1 | | | | | | | | | |
| | Methyl salicylate | | | | | | | | | | | | |
| | Hydrocortisone | | | | 1 | | | | | | 1 | | |
| | Aluminum chlorohydroxide | 0.1 | | | | | | | 2 | | | | |
| | Cortisone sulfate | | | | | | | | | 1 | | | |
| | Zinc undecylenic acid | | | | | | | | | 2 | | | |
| | Menthol | | 0.1 | | | | | 15 | | | | | |
| Propellant | LPG | 21.9 | 16.9 | 20.9 | 20.9 | 5.9 | 10 | 15 17.8 | 19.8 | 8.9 | 27.8 | 20.2 | 17.1 |
| | Dimethyl ether | | | | | 10 | 11.8 | | | | | | |
| | Total | 100 | 100 | 100 | 100 | 100 | 100 | 100 | 100 | 100 | 100 | 100 | 100 |
| Redispersion properties | | ⊙ | ⊙ | ⊙ | ⊙ | ⊙ | ⊙ | ⊙ | ⊙ | ⊙ | ⊙ | ⊙ | ⊙ |

What is claimed is:

1. A powder aerosol composition obtained by mixing a suspension comprising 5 to 60 wt % of at least one hydrophobic powdered substance having a pH in the range 5 to 9, 5 to 80 wt % of alcohol whose number of carbon atoms is in the range 1 to 7 and 5 to 80 wt % of water with 5 to 40 wt % of a propellant having a specific gravity lower than that of said suspension, the resulting suspension having a pH in the range of 5 to 9 and a viscosity in the range of 50 to 1000 cps.

2. A composition according to claim 1, wherein said suspension further comprises suitable amounts of at least one intentional medicine and/or at least one auxiliary agent.

3. A composition according to claim 1, wherein said hydrophobic powdered substance is suspended in said suspension in an amount preferably ranging from 20 to 30 wt %.

4. A composition according to claim 1, wherein said hydrophobic powdered substance is selected from the group consisting of talc, Celite, kaolin, red oxide, rice starch, bentonite and aluminum stearate.

5. A composition according to any one of claims 1 to 4, wherein said hydrophobic powdered substance has a particle size ranging from 70 to 325 mesh.

6. A composition according to claim 1, wherein said alcohol is added to said suspension in an amount preferably ranging from 25 to 35 wt %.

7. A composition according to claim 1 or 6, wherein said alcohol is either 95 vol % ethyl alcohol or isopropyl alcohol.

8. A composition according to claim 1, wherein said water is added to said suspension in an amount preferably ranging from 30 to 40 wt %.

9. A composition according to claim 2, wherein said intentional medicine and said auxiliary agent are an intentional medicine selected from the group consisting of basic aluminum chloride, methyl salicylate, hydrocortisone, aluminum chlorohydroxide, cortisone sulfate, zinc undecylenic acid and menthol, and an emollient medicine or germicide.

10. A composition according to claim 1 obtained by mixing 20 to 30 wt % of said propellant with 70 to 80 wt % of said suspension.

11. A composition according to claim 1 or 10, wherein said propellant is either a liquefied petroleum gas or dimethyl ether.

* * * * *